United States Patent
Yin et al.

(10) Patent No.: US 9,173,818 B2
(45) Date of Patent: Nov. 3, 2015

(54) METHOD FOR PREPARING STABLE-TYPE VITAMIN A MICROCAPSULES CONTINUOUSLY

(75) Inventors: Hong Yin, Hangzhou (CN); Jianfeng Chen, Beijing (CN); Zhirong Chen, Hangzhou (CN); Jiexin Wang, Beijing (CN); Yong Qi, Xinchang Shaoxing (CN); Hong Zhao, Beijing (CN); Lifang Shi, Xinchang Shaoxing (CN); Dan Qiu, Hangzhou (CN)

(73) Assignee: ZHEJIANG NHU COMPANY LTD, Yulin, Xinchang Shaoxing, Zhejiang (CN)

( * ) Notice: Subject to any disclaimer, the term of this patent is extended or adjusted under 35 U.S.C. 154(b) by 0 days.

(21) Appl. No.: 13/980,126

(22) PCT Filed: Mar. 25, 2011

(86) PCT No.: PCT/CN2011/072190
§ 371 (c)(1),
(2), (4) Date: Jul. 17, 2013

(87) PCT Pub. No.: WO2012/129765
PCT Pub. Date: Oct. 4, 2012

(65) Prior Publication Data
US 2014/0001662 A1  Jan. 2, 2014

(51) Int. Cl.
| | |
|---|---|
| A61J 3/07 | (2006.01) |
| A61K 9/00 | (2006.01) |
| B29B 9/12 | (2006.01) |
| A61K 9/16 | (2006.01) |
| A61K 9/50 | (2006.01) |
| A61K 31/07 | (2006.01) |
| A61K 9/51 | (2006.01) |

(52) U.S. Cl.
CPC ............ *A61J 3/07* (2013.01); *A61K 9/1652* (2013.01); *A61K 9/1694* (2013.01); *A61K 9/5036* (2013.01); *A61K 9/5089* (2013.01); *A61K 9/5161* (2013.01); *A61K 31/07* (2013.01)

(58) Field of Classification Search
CPC .............. A61K 2300/00; A61K 8/11; A61K 2800/412; A61K 8/732; A61K 9/5036; A61K 8/73; A61K 9/10; A61K 9/4833; A61K 2008/115; A61K 9/2866; A61K 9/4891; A61K 9/5042; A61K 9/5161; A23V 2002/00
USPC ......... 428/402–402.24, 403, 404, 407, 321.1, 428/474.4; 427/331, 389.9, 212, 427/213–213.36, 483, 256; 264/534, 5, 41, 264/4–4.7; 424/400, 408, 450, 451, 455, 424/93.7, 184.1, 497, 489, 501, 490, 491, 424/492, 493, 494, 495
See application file for complete search history.

(56) References Cited

U.S. PATENT DOCUMENTS

| | | | | |
|---|---|---|---|---|
| 5,648,091 | A * | 7/1997 | Sarama et al. ................. | 424/451 |
| 2012/0018912 | A1* | 1/2012 | Chen et al. .................... | 264/5 |

FOREIGN PATENT DOCUMENTS

| | | |
|---|---|---|
| CN | 1965657 A | 5/2007 |
| CN | 101214219 A | 7/2008 |
| CN | 101513394 A | 8/2009 |
| CN | 101574632 A | 11/2009 |
| CN | 101744790 A | 6/2010 |

OTHER PUBLICATIONS

Xu Xinde et al., "Compression and consolidation behavior of some kinds of β-carotene microencapsulated powder," Journal of Chemical Industry and Engineering (China), vol. 58, No. 2, pp. 452-459, (Feb. 2007).
International Search Report (in Chinese with English translation) for PCT/CN2011/072190, mailed Jan. 5, 2012; ISA/CN.

* cited by examiner

*Primary Examiner* — James J Seidleck
*Assistant Examiner* — S. Camilla Pourbohloul
(74) *Attorney, Agent, or Firm* — Harness, Dickey & Pierce, P.L.C.

(57) ABSTRACT

A method for continuously preparing stable-type vitamin A microcapsules is disclosed. The method comprises the following steps: adding vitamin A crystals and an antioxidant into a crystal melter continuously according to a certain ratio under the protection of nitrogen to prepare vitamin A melting oil containing the antioxidant; pumping the above melting oil into a high gravity rotary packed bed emulsifier with a liquid distributor by a pump, and pumping aqueous solution containing gellable modified starch into the above high gravity rotary packed bed emulsifier after deoxidation treatment to obtain vitamin A emulsion at the outlet of the high gravity rotary packed bed emulsifier; and atomizing and spraying the emulsion continuously in a cooled starch bed for granulating, and performing fluidization drying and gelation treatment in a fluidized bed by taking nitrogen as a drying medium to obtain the stable-type vitamin A microcapsules. Above method has the advantage of capability of continuous production, and has good embedding effect due to adopting the gellable modified starch, granulating and gelation treatment, thus the product has good storage stability.

2 Claims, No Drawings

METHOD FOR PREPARING STABLE-TYPE VITAMIN A MICROCAPSULES CONTINUOUSLY

CROSS-REFERENCE TO RELATED APPLICATIONS

This application is a 371 U.S. National Stage of International Application No. PCT/CN2011/072190, filed on Mar. 25, 2011, the disclosure of which is incorporated herein by reference in its entirety.

FIELD OF THE INVENTION

The present invention relates to a method for continuously preparing stabilized vitamin A microcapsules, specifically to the continuous preparation of stabilized vitamin A microcapsules by using high gravity rotary packed bed emulsifier.

BACKGROUND OF THE INVENTION

Vitamin A, which is a fat-soluble vitamin, is easily soluble in organic solvent and fat, and is insoluble in water. Vitamin A is perishable when exposed to light, heat, acid, or oxidant, so it is generally required to be prepared into a microcapsule form to use it.

The microcapsulation of vitamin A is generally, first heating vitamin A crystals, accessory oil and aqueous solution containing protective colloid together, emulsifying, and then spray drying the emulsion, to obtain the microcapsule.

China patent CN1965657(A) describes a method for preparing vitamin A microcapsules, said method is adding vitamin A oil into a solution of modified starch pre-formulated several hours earlier, and dispersing and emulsifying at high speed with a rotating speed of 5000~20000 rpm, then homogenizing twice at 10~40 MPa at room temperature, and finally centrifugal spray drying, to obtain the vitamin A microcapsule. Due to the fine particle size of the obtained product, it is mainly used for the fortification of flour.

China patent CN101214219(A) reports a method for preparing vitamin A, vitamin E microcapsules, and the emulsifying process thereof employs 10000~20500 rpm high-speed shearing, and homogenization at 40~60 MPa for 3 times is required, and then the microcapsule is prepared by spray-drying.

The above-mentioned method for preparing vitamin A microcapsules by high-speed shearing emulsification plus high-pressure homogenization and then spray-drying, has the following insurmountable problems:

1) the emulsifying process is carried out batchwise in an open environment, and the emulsifying time for a single batch is long, and when emulsifying, the temperature at the shearing site is high, which causes vitamin A perishable;

2) the motor power required by the high speed shearing machine and the high pressure homogenizer is high, and the energy consumption is high;

3) due to the batchwise operation, during the spray-drying process after completing the emulsification, the emulsion is prone to stratify, and the gathered small oil bead is easily coalesced into large particles, thus affecting the embedding effect and the bioavailability of the final product.

4) It is difficult for vitamin A to disperse into the microcapsule in nano-scale dimensions by the high pressure homogenization, thus affecting the use thereof in certain products.

In view of the above-mentioned problems, the present inventors have proposed a method for continuously preparing nano-dispersed vitamin A microcapsule in CN101513394. In this method, vitamin A crystals are first ground with antioxidant and solvent into a dispersion liquid of vitamin A, then the above-mentioned dispersion liquid is cooled by a pump after pre-heating and warming to dissolve, then pumped into a high gravity rotary bed crystallization device, meanwhile an aqueous solution containing protective colloid is pumped into the same high gravity rotary bed crystallization device, to obtain a nano-dispersed dispersion liquid of vitamin A at the outlet. The dispersion liquid is spray-dried in a spray dryer equipped with a fluidized cooling device, to obtain the nano-dispersed microcapsule of vitamin A. This invention employs a high gravity rotary bed crystallization device as the means for the nano-crystallization of vitamin A, so that the bioavailability of vitamin A is increased, and the applicability of the product is broadened.

However, vitamin A is a fat-soluble vitamin with poor stability, even after the microencapsulation by spray-drying, the effective content thereof will still significantly decrease during the storage, due to the effects of light, heat, oxidant, and acid. Through further studies, we found that, if avoiding the long-time heating and minimizing the chances to contact with oxygen during the microcapsulation of vitamin A, meanwhile increasing the oxygen-preventing and water-preventing measures of the outer layer of microcapsule, the stability of vitamin A can be effectively increased.

SUMMARY OF THE INVENTION

The purpose of the present invention is to provide a method for continuously preparing stabilized vitamin A microcapsules, in view of the deficiencies of the production technology of vitamin A microcapsules.

The method for continuously preparing stabilized vitamin A microcapsules comprises the following steps:

1) under the protection of nitrogen gas, continuously adding vitamin A crystals and an antioxidant in a weight ratio of 100:1~5 into a crystal melter, melting at 65~75° C., to form vitamin A melting oil containing the antioxidant;

2) dissolving gellable modified starch in water at 65~75° C., to form aqueous solution of 30~40% modified starch, and deoxygenating at a vacuum of −0.07~−0.08 MPa for 1~2 hours;

3) pumping the vitamin A melting oil into a high gravity rotary packed bed emulsifier equipped with a liquid distributor; meanwhile, pumping the deoxygenated aqueous solution of modified starch into the same high gravity rotary packed bed emulsifier, to obtain a vitamin A emulsion at the outlet, and the weight ratio of the vitamin A melting oil to the aqueous solution of modified starch is 1:3~9;

4) continuously atomizing and spraying the vitamin A emulsion into a cooled starch bed for granulation, then performing fluidized drying and gelation treatment in a fluidized bed at 65~75° C. using nitrogen gas as drying medium, to obtain the stabilized vitamin A microcapsules.

The antioxidant is ethoxy quinoline, tocopherol, BHT or BHA.

The high gravity rotary packed bed emulsifier is equipped with a liquid distributor, and the packing stuff is wire mesh, and the rotating speed is 1500~2500 rpm.

The present invention has the following advantageous effects in comparison with the prior art:

1) employing the gellable modified starch as the main embedding material, then performing spray granulation, fluidized drying and gelation treatment, thus producing double protections to the product, which has a good embedding effect, and is not easy to absorb moisture;

2) employing high gravity rotary packed bed emulsifier to continuously emulsify, the particle size of the vitamin A in the emulsion is uniform, so as to avoid the production of large crystals which have a low bioavailability;

3) the sufficient nitrogen gas protection and deoxygenating measures during the producing process ensure that vitamin A does not deteriorate during the production process, such that not only the yield of the microcapsulation process is increased, but also the storage stability of the product is increased.

The present invention is described in detail in conjunction with the following examples.

DETAILED EMBODIMENTS

Example 1

Under the protection of nitrogen gas, vitamin A crystals (at 10 Kg/hour) and antioxidant ethoxy quinoline (at 0.5 Kg/hour) were added into a specially-made crystal melter, and the crystals were allowed to melt at 65° C., to obtain 10.5 Kg/hour vitamin A melting oil.

567 Kg gellable modified starch was dissolved in 1323 Kg water at 65° C., and formulated into an aqueous solution of 30% modified starch, and degassed at −0.08 MPa for 2 hours.

The above-mentioned vitamin A melting oil was pumped at a flow rate of 10.5 Kg/hour into a high gravity rotary packed bed emulsifier equipped with a liquid distributor, with a rotating speed of 1500 rpm, meanwhile the aqueous solution of modified starch after deoxygenation was pumped at a flow rate of 94.5 Kg/hour into the same high gravity rotary packed bed emulsifier, and a vitamin A emulsion was obtained at the outlet.

The above-mentioned vitamin A emulsion was continuously atomized and sprayed into a cooled starch bed for the granulation for 20 hours, to obtain about 2800 Kg wet vitamin A microcapsules.

The above-mentioned wet vitamin A microcapsules were transferred into a fluidized bed, and performed fluidized drying and gelation treatment using 65° C. hot nitrogen gas, to finally obtain 1010 Kg vitamin A microcapsules. Through HPLC analysis, the content of vitamin A was 19.62%, and the yield of the microcapsules was 99.08%. After storing for 2 years at normal temperature, the content was 19.05%, and the retention rate of vitamin A was 97.1%.

The gellable modified starch is CAPSUL 2330 manufactured by National Starch (U.S. National Starch Co., Ltd.).

Example 2

Under the protection of nitrogen gas, vitamin A crystals (at 10 Kg/hour) and antioxidant tocopherol (at 0.3 Kg/hour) were added into a specially-made crystal melter, and the crystals were allowed to melt at 70° C., to obtain 10.3 Kg/hour vitamin A melting oil.

247.2 Kg gellable modified starch was dissolved in 370.8 Kg water at 75° C., and formulated into an aqueous solution of 40% modified starch, and degassed at −0.07 MPa for 1 hour.

The above-mentioned vitamin A melting oil was pumped at a flow rate of 10.3 Kg/hour into a high gravity rotary packed bed emulsifier equipped with a liquid distributor, with a rotating speed of 2500 rpm, meanwhile the aqueous solution of modified starch after deoxygenation was pumped at a flow rate of 30.9 Kg/hour into the same high gravity rotary packed bed emulsifier, and a vitamin A emulsion was obtained at the outlet.

The above-mentioned vitamin A emulsion was continuously atomized and sprayed into a cooled starch bed for the granulation for 20 hours, to obtain about 1100 Kg wet vitamin A microcapsules.

The above-mentioned wet vitamin A microcapsules were transferred into a fluidized bed, and performed fluidized drying and gelation treatment using 75° C. hot nitrogen gas, to finally obtain 548 Kg vitamin A microcapsules. Through HPLC analysis, the content of vitamin A was 36.05%, and the yield of the microcapsules was 98.78%. After storing for 2 years at normal temperature, the content was 34.72%, and the retention rate of vitamin A was 96.3%.

Example 3

Under the protection of nitrogen gas, vitamin A crystals (at 10 Kg/hour) and antioxidants BHT (at 0.05 Kg/hour) and BHA (at 0.05 Kg/hour) were added into a specially-made crystal melter, and the crystals were allowed to melt at 75° C., to obtain 10.1 Kg/hour vitamin A melting oil.

424.2 Kg gellable modified starch was dissolved in 787.8 Kg water at 70° C., and formulated into an aqueous solution of 35% modified starch, and degassed at −0.075 MPa for 1.5 hours.

The above-mentioned vitamin A melting oil was pumped at a flow rate of 10.1 Kg/hour into a high gravity rotary packed bed emulsifier equipped with a liquid distributor, with a rotating speed of 2000 rpm, meanwhile the aqueous solution of modified starch after deoxygenation was pumped at a flow rate of 60.6 Kg/hour into the same high gravity rotary packed bed emulsifier, and a vitamin A emulsion was obtained at the outlet.

The above-mentioned vitamin A emulsion was continuously atomized and sprayed into a cooled starch bed for the granulation for 20 hours, to obtain about 1800 Kg wet vitamin A microcapsules.

The above-mentioned wet vitamin A microcapsules were transferred into a fluidized bed, and performed fluidized drying and gelation treatment using 70° C. hot nitrogen gas, to finally obtain 776 Kg vitamin A microcapsules. Through HPLC analysis, the content of vitamin A was 25.53%, and the yield of the microcapsules was 99.06%. After storing for 2 years at normal temperature, the content was 24.69%, and the retention rate of vitamin A was 96.7%.

Comparative Example 1

200 Kg vitamin A crystals and 10 Kg ethoxy quinoline were placed into an oil melting kettle, and the crystals were allowed to melt at 65° C., to obtain 210 Kg vitamin A melting oil.

567 Kg common modified starch and 260 Kg dextrin were dissolved in 1930 Kg water at 65° C., and formulated into an aqueous solution of 30% modified starch.

The above-mentioned aqueous solution of modified starch was placed into a emulsifying kettle equipped with a high shear emulsifier, and the above-mentioned vitamin A melting oil was added into the emulsifying kettle under high speed shearing, and further emulsified by shearing for 1 hour after the addition. Then, under a condition of low speed shearing, the above-mentioned emulsion was spray-dried at a flow rate of 300 Kg/hour, and the spray was completed 9.9 hours later. Finally, 1006 Kg vitamin A microcapsules were obtained. Through HPLC analysis, the content of vitamin A was 18.86%, and the yield of the microcapsules was 94.98%.

After storing for 2 years at normal temperature, the content was 17.07%, and the retention rate of vitamin A was 90.5%.

Comparative Example 2

200 Kg vitamin A crystals and 6 Kg tocopherol were placed into an oil melting kettle, and the crystals were allowed to melt at 70° C., to obtain 206 Kg vitamin A melting oil.

247.2 Kg common modified starch and 115 Kg dextrin were dissolved in 543 Kg water at 75° C., and formulated into an aqueous solution of 40% modified starch.

The above-mentioned aqueous solution of modified starch was placed into a emulsifying kettle equipped with a high shear emulsifier, and the above-mentioned vitamin A melting oil was added into the emulsifying kettle under high speed shearing, and further emulsified by shearing for 1 hour after the addition. Then, under a condition of low speed shearing, the above-mentioned emulsion was spray-dried at a flow rate of 300 Kg/hour, and the spray was completed 3.7 hours later. Finally, 550 Kg vitamin A microcapsules were obtained. Through HPLC analysis, the content of vitamin A was 34.62%, and the yield of the microcapsules was 95.20%. After storing for 2 years at normal temperature, the content was 30.88%, and the retention rate of vitamin A was 89.2%.

Comparative Example 3

200 Kg vitamin A crystals, 1 Kg BHT and 1 Kg BHA were placed into an oil melting kettle, and the crystals were allowed to melt at 75° C., to obtain 202 Kg vitamin A melting oil.

424.2 Kg common modified starch and 180 Kg dextrin were dissolved in 1122 Kg water at 70° C., and formulated into an aqueous solution of 35% modified starch.

The above-mentioned aqueous solution of modified starch was placed into a emulsifying kettle equipped with a high shear emulsifier, and the above-mentioned vitamin A melting oil was added into the emulsifying kettle under high speed shearing, and further emulsified by shearing for 1 hour after the addition. Then, under a condition of low speed shearing, the above-mentioned emulsion was spray-dried at a flow rate of 300 Kg/hour, and the spray was completed 6.4 hours later. Finally, 780 Kg vitamin A microcapsules were obtained. Through HPLC analysis, the content of vitamin A was 24.49%, and the yield of the microcapsules was 95.52%. After storing for 2 years at normal temperature, the content was 22.24%, and the retention rate of vitamin A was 90.8%.

The invention claimed is:

1. A method for continuously preparing stabilized vitamin A microcapsules, characterized in that the method comprises the following steps:
    1) under the protection of nitrogen gas, continuously adding vitamin A crystals and an antioxidant in a weight ratio of 100:1~5 into a crystal melter, melting at 65~75° C., to form vitamin A melting oil containing the antioxidant;
    2) dissolving gellable modified starch in water at 65~75° C., to form aqueous solution of 30~40% modified starch, and deoxygenating at a vacuum of −0.07~−0.08 MPa for 1~2 hours;
    3) pumping the vitamin A melting oil into a high gravity rotary packed bed emulsifier equipped with a liquid distributor; meanwhile, pumping the deoxygenated aqueous solution of modified starch into the same high gravity rotary packed bed emulsifier, to obtain a vitamin A emulsion at the outlet, and the weight ratio of the vitamin A melting oil to the aqueous solution of modified starch is 1:3~9; and
    4) continuously atomizing and spraying the vitamin A emulsion into a cooled starch bed for granulation, then performing fluidized drying and gelation treatment in a fluidized bed at 65~75° C. using nitrogen gas as drying medium, to obtain the stabilized vitamin A microcapsule,
    wherein the antioxidant is ethoxy quinolone, tocopherol, BHT or BHA.

2. The method for continuously preparing stabilized vitamin A microcapsules according to claim 1, characterized in that the high gravity rotary packed bed emulsifier is equipped with a liquid distributor, and the packing stuff is wire mesh, and the rotating speed is 1500~2500 rpm.

* * * * *